(12) United States Patent
Tanaka et al.

(10) Patent No.: US 10,048,214 B2
(45) Date of Patent: Aug. 14, 2018

(54) ROLLING ELEMENT INSPECTION METHOD, ROLLING ELEMENT MANUFACTURING METHOD, AND ROLLING ELEMENT

(75) Inventors: Yutaka Tanaka, Kuwana (JP); Katsutoshi Muramatsu, Kuwana (JP); Hiroaki Suzuki, Kuwana (JP); Daichi Ito, Kuwana (JP); Masayuki Nozaki, Kuwana (JP)

(73) Assignee: NTN CORPORATION, Osaka (JP)

( * ) Notice: Subject to any disclaimer, the term of this patent is extended or adjusted under 35 U.S.C. 154(b) by 215 days.

(21) Appl. No.: 14/241,043

(22) PCT Filed: Jul. 27, 2012

(86) PCT No.: PCT/JP2012/069155
§ 371 (c)(1),
(2), (4) Date: Feb. 25, 2014

(87) PCT Pub. No.: WO2013/031450
PCT Pub. Date: Mar. 7, 2013

(65) Prior Publication Data
US 2014/0205063 A1    Jul. 24, 2014

(30) Foreign Application Priority Data

Aug. 26, 2011  (JP) .................. 2011-184878

(51) Int. Cl.
*G01N 23/083* (2018.01)
*G01M 13/04* (2006.01)
(Continued)

(52) U.S. Cl.
CPC ............. *G01N 23/04* (2013.01); *F16C 33/30* (2013.01); *G01M 13/04* (2013.01); *G01N 23/083* (2013.01); *G01N 2223/646* (2013.01)

(58) Field of Classification Search
None
See application file for complete search history.

(56) References Cited

U.S. PATENT DOCUMENTS 4,149,247 A * 4/1979 Pavkovich ............. A61B 6/032
378/14
4,672,650 A * 6/1987 Masanobu ............. A61B 6/583
378/4
(Continued)

FOREIGN PATENT DOCUMENTS

EP    2 302 243 A1    3/2011
JP    5-281160 A    10/1993
(Continued)

OTHER PUBLICATIONS

Takashio, S. et al. "Case of Analyzing a Three Dimensional Actual Article Model Obtained from an X Ray CT Image," Image Lab, Japan Industrial Publishing Co., Ltd., May 1, 2005; vol. 16, No. 5, pp. 19-21; with partial English translation.
(Continued)

*Primary Examiner* — Wyatt Stoffa
*Assistant Examiner* — James Choi
(74) *Attorney, Agent, or Firm* — McDermott Will & Emery LLP

(57) ABSTRACT

An inspection method of a rolling element includes the steps of: projecting an X-ray from a light source to a rolling element, detecting the X-ray passing through the rolling element by a detector, calculating data of the detected X-ray to form an image, and detecting a defect in the rolling element based on the image. At the step of projecting an X-ray, the light source rotates relatively around the rolling element while the X-ray is projected to an entire region of the rolling element facing the light source. At the step of
(Continued)

forming an image, data of the X-ray for one circuit around the rolling element is calculated to generate the image.

8 Claims, 2 Drawing Sheets

(51) Int. Cl.
*F16C 33/30* (2006.01)
*G01N 23/04* (2018.01)

(56) References Cited

U.S. PATENT DOCUMENTS

| | | | | |
|---|---|---|---|---|
| 5,473,655 | A * | 12/1995 | Hu | G01N 23/046 378/4 |
| 6,341,153 | B1 * | 1/2002 | Rivera | G01N 23/046 378/10 |
| 2006/0067461 | A1 * | 3/2006 | Yin | G06T 11/005 378/5 |
| 2007/0238957 | A1 * | 10/2007 | Yared | A61B 5/0059 600/407 |
| 2008/0205596 | A1 | 8/2008 | Kato | |
| 2009/0003516 | A1 | 1/2009 | Chen et al. | |
| 2009/0304142 | A1 * | 12/2009 | Ruimi | A61B 6/032 378/7 |
| 2017/0365077 | A1 * | 12/2017 | Monkawa | G01B 15/04 |

FOREIGN PATENT DOCUMENTS

| | | | |
|---|---|---|---|
| JP | 05281160 | A * | 10/1993 |
| JP | 5322802 | A | 12/1993 |
| JP | 05332802 | A * | 12/1993 |
| JP | 8-146137 | A | 6/1996 |
| JP | 3202311 | B2 | 6/2001 |
| JP | 2001201465 | A | 7/2001 |
| JP | 2002-243662 | A | 8/2002 |
| JP | 2005-283547 | A | 10/2005 |
| JP | 2010-054500 | A | 11/2010 |
| JP | 2010-286069 | A | 12/2010 |
| JP | 2011-038881 | A | 2/2011 |

OTHER PUBLICATIONS

Flynn, M. J., et al. "Microfocus X-ray Sources for 3D Microtomography" Nuclear Instruments & Methods in Physics Research A, 353; pp. 312-315; 1994.
Kondo, N. et al. "Evaluation of Joined Silicon Nitride by X-ray Computed Tomography (X-ray CT)," Journal of the Ceramic Society of Japan; vol. 118, No. 12; pp. 1192-1194; 2010.
European Extended Search Report issued in corresponding European Patent Application No. 12827264.8, dated Mar. 4, 2015; 7 pages in English language.
Japanese Notice of Grounds of Rejection issued in corresponding Japanese Patent Application No. 2011-184878, dated Mar. 10, 2015; 6 pages with English translation.
International Search Report issued in Application No. PCT/JP2012/069155 dated Sep. 25, 2012.

* cited by examiner

ROLLING ELEMENT INSPECTION METHOD, ROLLING ELEMENT MANUFACTURING METHOD, AND ROLLING ELEMENT

CROSS-REFERENCE TO RELATED APPLICATIONS

The present application is the U.S. National Phase of PCT/JP2012/069155 dated Jul. 27, 2012 which claims priority from Japanese Patent Application No. 2011-184878 filed Aug. 26, 2011 the subject matter of each is incorporated herein by reference in entirety.

TECHNICAL FIELD

The present invention relates to a rolling element inspection method, a rolling element manufacturing method, and a rolling element. More particularly, the present invention relates to a method of inspecting a rolling element made of ceramics, used as a rolling element of a rolling bearing, for example, a method of manufacturing the rolling element, and the rolling element.

BACKGROUND ART

In recent years, the need arises for a shaft such as the main spindle of a working machine to exhibit higher rotation and higher accuracy. There is a growing demand for a rolling element made of ceramics that is light and highly tough as a rolling element of a rolling bearing that supports such a shaft. A rolling element made of ceramics has high insulation. Therefore, the potential of a rolling element of a bearing for use in power generators and motors is high. There is also the potential for use in transportation machines such as aircrafts and automobiles by virtue of its lightweight property as compared to a steel ball that is the general rolling element of a bearing.

By the demand of high reliability in rolling bearings, 100% inspection is required in the manufacturing of rolling elements made of ceramics to detect any defect in the material and work. The size of the defect to be detected is generally greater than or equal to 20 μm, depending upon the material strength and the like.

A scratch on the surface of the rolling element, a defect in the inclusion and the like may be detected by an appearance inspection through visual confirmation, the method of inspecting the reflected state of light from the surface of a rolling element using an optical system, and the like. Since the time required for such inspection is short according to these methods, they can be employed in mass production processes.

However, in rolling elements made of ceramics, the durability may be degraded even in the case where there is a defect, not only at the surface, but also inside. Therefore, the inspection for a defect must be performed for the entire interior in addition to the surface of the rolling element.

As a method of detecting a defect present inside a component made of ceramics, there is proposed a method including the steps of applying integration processing on an image obtained by X-ray transmission, and differentiating the integration-processed image to detect an internal defect (for example, refer to Japanese Patent Laying-Open No. 8-146137 (PTD 1)). However, this method requires a long period of time for image pickup since pictures for the integration processing must be taken. It is therefore difficult to employ this method in the inspection for the mass production of rolling elements.

There is also known a method of evaluating the porosity distribution of silicon nitride sintered body using X-ray CT (Computed Tomography) (for example, refer to Japanese Patent Laying-Open No. 2001-201465 (PTD 2)). According to this method, a pore of approximately 10 μm can be detected. However, this method also requires a significant period of time for image pickup. Therefore, it is difficult to employ this method in the inspection method for mass production of rolling elements.

There is additionally known a method of measuring the porosity distribution in a ceramic structure by driving an X-ray source and a detector helically in a scanning operation using medical X-ray CT (for example, refer to Japanese Patent Laying-Open No. 2005-283547 (PTD 3)). This method allows a ceramic structure to be inspected in a relatively short time. However, the aforementioned helical scanning operation by an X-ray source and detector requires the inspection to be carried out based on images corresponding to a predetermined distance. The entirety of the subject of inspection cannot be inspected without omission. Therefore, it cannot be said that this method is appropriate for a rolling element made of ceramics that requires high reliability.

CITATION LIST

Patent Document

PTD 1: Japanese Patent Laying-Open No. 8-146137
PTD 2: Japanese Patent Laying-Open No. 2001-201465
PTD 3: Japanese Patent Laying-Open No. 2005-283547

SUMMARY OF INVENTION

Technical Problem

Although various types of methods are proposed for inspecting an internal defect (for example, an inclusion, hole, and the like) in a structure made of ceramics as set forth above, they have problems such as the inspection is too time-consuming, the entirety of the interior of the structure cannot be inspected without omission, and the like. They are insufficient for the method of inspecting a rolling element made of ceramics.

In view of the foregoing, an object of the present invention is to provide a rolling element inspection method allowing a rolling element made of ceramics to be inspected entirely without omission and in a short period of time, a rolling element manufacturing method employing the inspection method, and a rolling element manufactured by the manufacturing method.

Solution to Problem

A rolling element inspection method of the present invention is directed to a method of inspecting a rolling element made of ceramics. The inspection method includes the steps of projecting an X-ray from a light source to a rolling element, detecting the X-ray passing through the rolling element, calculating data of the detected X-ray to generate an image, and detecting a defect in the rolling element based on the image. At the step of projecting an X-ray, the light source rotates relatively around the rolling element while an X-ray is projected to an entire region of the rolling element facing the light source. At the step of generating an image, the data of the X-ray for one circuit around the rolling element is calculated to generate an image.

In the rolling element inspection method of the present invention, the light source rotates relatively around a rolling element while an X-ray is projected to an entire region of the rolling element facing the light source, and data of the X-ray for one circuit around the rolling element is calculated to generate an image. Therefore, the entirety of the rolling element made of ceramics can be inspected without omission, differing from the case where images picked up at a predetermined distance are integrated. Moreover, since an image is generated based on data of the X-ray for one circuit around the rolling element, the inspection can be performed in a short period of time, differing from the case where images for the integration processing are picked up over a significant period of time. Thus, according to the rolling element inspection method of the present invention, a rolling element made of ceramics can be inspected entirely without omission and in a short period of time.

In the step of projecting an X-ray in the rolling element inspection method set forth above, an X-ray may be projected from a light source having a focal point size less than or equal to 10 μm.

Accordingly, blurring is reduced even if the rolling element approaches the focal point of the light source, allowing high resolution to be obtained. As a result, a minute defect, for example a defect having a size of approximately 20 μm, can be readily detected.

In the step of projecting an X-ray in the rolling element inspection method set forth above, an X-ray spreading conically from the light source may be projected to the rolling element. Accordingly, the entire region of the rolling element facing the light source can be readily irradiated with an X-ray. Particularly in the case where the focal point size of the light source is reduced down to less than or equal to 10 μm, the entire region of the rolling element facing the light source can be readily irradiated with an X-ray by projecting the X-ray to the rolling element so as to spread conically.

In the rolling element inspection method set forth above, the ceramics may have silicon nitride or sialon as the main component.

For a rolling element having ceramics formed of atoms of low atomic number such as silicon nitride or sialon as the main component, internal inspection by transmitting an X-ray is facilitated. Therefore, the rolling element inspection method of the present invention is suitable to the inspection of a rolling element formed of ceramics with silicon nitride or sialon as the main component In the rolling element inspection method set forth above, an internal defect may be detected in the step of detecting a defect.

In the rolling element inspection method of the present invention, an X-ray passing through a rolling element is detected to implement the inspection. Therefore, the rolling element inspection method of the present invention is suitable for detecting an internal defect that is difficult to be detected in the aforementioned appearance inspection by visual confirmation.

In the step of detecting a defect in the rolling element inspection method set forth above, a defect having a size of at least 20 μm may be detected. Accordingly, sufficient accuracy can be ensured for a method of inspecting a rolling element made of ceramics.

In the rolling element inspection method set forth above, the defect detected in the step of detecting a defect may be a metal inclusion or a hole.

The metal inclusion or hole may have a serious effect on the durability and the like of a rolling element made of ceramics. By detecting such defects, an inspection allowing the reliability of the rolling element to be further improved can be implemented.

A rolling element manufacturing method according to the present invention includes the steps of producing a rolling element made of ceramics, and inspecting the rolling element. In the step of inspecting the rolling element, the rolling element is inspected by the above-described rolling element inspection method of the present invention.

By employing a rolling element inspection method of the present invention allowing a rolling element to be inspected entirely without omission and in a short period of time, the rolling element manufacturing method of the present invention allows a highly-reliable rolling element made of ceramics to be manufactured efficiently.

A rolling element according to the present invention is manufactured by the above-described rolling element manufacturing method of the present invention. By the rolling element of the present invention, there can be provided a rolling element made of ceramics, highly-reliable and having the production cost suppressed by the efficient manufacturing.

Advantageous Effects of Invention

According to a rolling element inspection method, a rolling element manufacturing method, and a rolling element of the present invention, there can be provided a rolling element inspection method that allows a rolling element made of ceramics to be inspected entirely without omission and in a short period of time, a rolling element manufacturing method employing the inspection method, and a rolling element manufactured by the manufacturing method.

DESCRIPTION OF EMBODIMENTS

Figure 1:
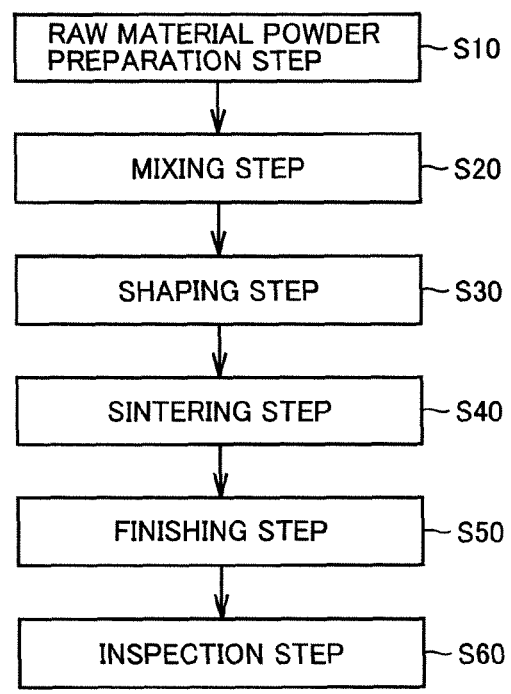
FIG. 1 is a flowchart schematically representing a manufacturing method of a rolling element made of ceramics.

Embodiments of the present invention will be described hereinafter based on the drawings. In the drawings, the same or corresponding elements have the same reference characters allotted, and description thereof will not be repeated.

In a rolling element manufacturing method according to an embodiment of the present invention with reference to FIG. 1, a raw material powder preparation step is executed as step S10. At step S10, raw material powder such as silicon nitride, sialon, and the like is prepared.

Then, a mixing step is executed as step S20. At step S20, a sintering agent prepared separately is added and mixed with the raw material powder prepared at, for example, step S10. In the case where a rolling element is to be manufactured by mixing a plurality of types of raw material powder, such raw material powder can be mixed at this step S20. In the case where a sintering agent is not employed and a rolling element is to be manufactured from one type of raw material powder, step S20 can be omitted.

Then, a shaping step is executed as step S30. At step S30, the above-described raw material powder, a mixture of raw material powder, or a mixture of raw material powder and sintering agent is shaped to a substantial form of a rolling element. Specifically, by applying a shaping method such as press-forming, casting, extrusion molding, granulation, and the like to the powder, a compact shaped to substantially the form of a rolling element such as a ball or roller can be produced.

Then, a sintering step is executed as step S40. At step S40, the compact is sintered to produce a sintered compact. This step S40 may be executed by employing pressure sintering such as hot press (HP) and hot isostatic press (HIP), or by pressureless sintering. For the aforementioned sintering heating method, electromagnetic wave heating such as by microwaves or millimeter waves may be employed in addition to heating using a heater.

Then, a finishing step is executed as step S50. At step S50, the surface of the sintered compact produced at step S40 is worked to execute a finishing process in which a region including the surface is removed. Thus, a ceramics rolling element is completed.

Then, an inspection step is executed as step S60. At step S60, the above-described ceramics rolling element is inspected by a rolling element inspection method according to the present embodiment that will be described hereinafter.

Figure 2:
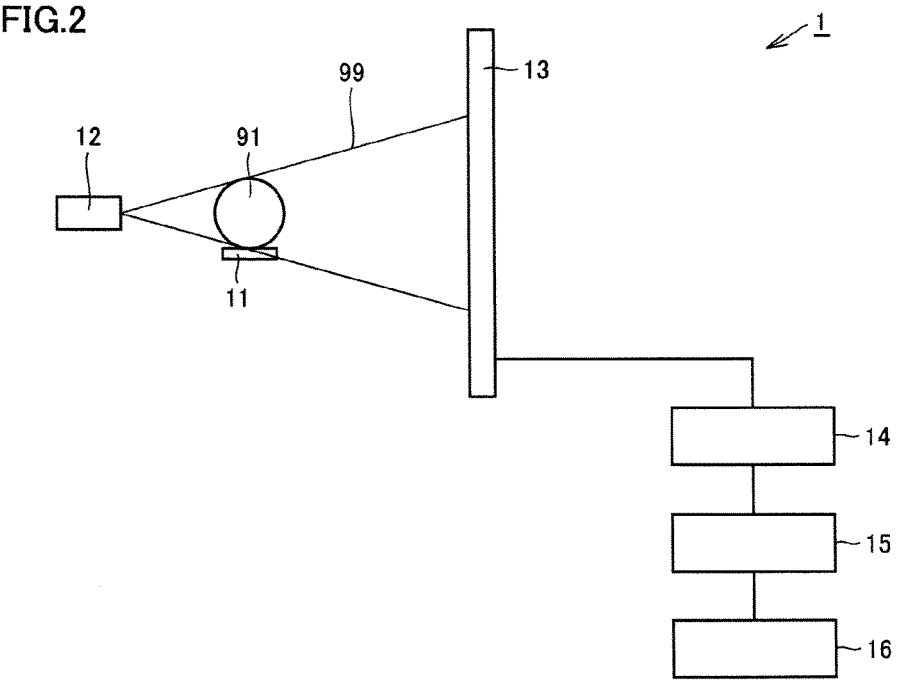
FIG. 2 is a schematic diagram of a configuration of a device to implement a rolling element inspection method of the present invention.
Figure 3:
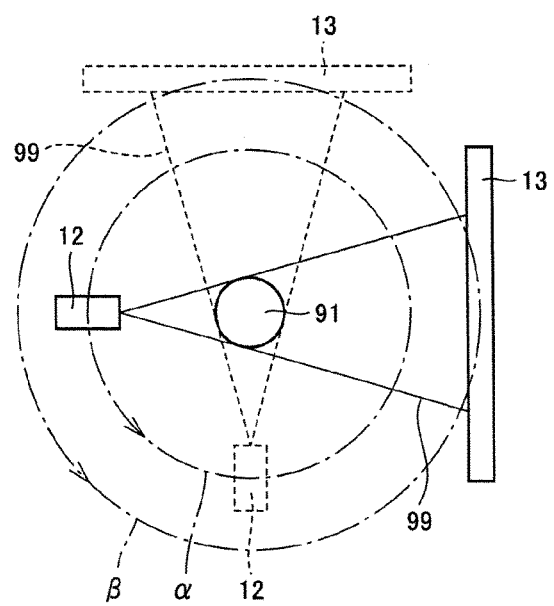
FIG. 3 is a diagram to describe an operation of a light source and a detector.

First, an inspection device employed in the rolling element inspection method of the present embodiment will be described with reference to FIGS. 2 and 3. FIG. 2 is a sectional view including the rotation axis of the light source, whereas FIG. 3 is a sectional view perpendicular to the rotation axis of the light source. Referring to FIG. 2, an inspection device 1 of the present embodiment corresponding to X-ray CT includes a holder 11 for holding a rolling element 91 such as a ball or roller, a light source 12 for projecting an X-ray 99 to rolling element 91 held by holder 11, and a detector 13 arranged at a side opposite to light source 12 about rolling element 91 held by holder 11, and detecting an X-ray passing through rolling element 91. For detector 13, a semiconductor flat panel detector, for example, may be employed. Light source 12 and detector 13 can rotate about rolling element 91 held by holder 11 while maintaining a positional relationship relative to each other, as shown in FIG. 3.

Inspection device 1 further includes a calculation unit 14 connected to detector 13 for calculating data of an X-ray detected by detector 13, an image formation unit 15 connected to calculation unit 14 for forming an image based on the calculated result at calculation unit 14, and a defect detector 16 connected to image formation unit 14 for detecting a defect in rolling element 91 based on the formed image.

Next, an inspection method of rolling element 91 according to the present embodiment using inspection device 1 set forth above will be described hereinafter. In the inspection method of the present embodiment with reference to FIGS. 2 and 3, first, rolling element 91 that is the subject of inspection is set at holder 11. For rolling element 91, an element with ceramics as the main component, formed of atoms of low atomic number and light in weight such as silicon nitride or sialon can be employed.

Next, X-ray 99 is projected from light source 12 to rolling element 91 held by holder 11. At this stage, the entirety of the region of rolling element 91 facing light source 12 is irradiated with X-ray 99, as shown in FIGS. 2 and 3. The projected X-ray 99 passes through rolling element 91 to be detected by detector 13. Projection of X-ray 99 from light source 12 and detection of X-ray 99 by detector 13 are implemented while the positional relationship between light source 12 and detector 13 is maintained by light source 12 rotating along arrow α about rolling element 91, as shown in FIG. 3, and detector 13 rotating along arrow β.

Referring to FIG. 2, data of X-ray 99 detected by detector 13 is calculated at calculation unit 14. Based on the calculated result, an image is formed at image formation unit 15. This image is generated by the calculation of data of X-ray 99 for one circuit around rolling element 91.

Based on the formed image, a defect in rolling element 91, for example an internal defect such as a metal inclusion and/or hole, is detected by defect detector 16. Although the size of the detected defect is preferably to the smallest possible degree, a defect having a size of at least 20 μm is preferably detected. In order to achieve such high detection sensitivity, preferably the method of performing X-ray projection and detection using a micro focus X-ray source for light source 12, having the focal point size less than or equal to 10 μm, specifically approximately 5 μm, using X-ray 99 spreading conically from light source 12, i.e. volume measurement by the so-called cone beam scanning, is implemented.

In the inspection method of rolling element 91 of the present embodiment, light source 12 rotates relative to and around rolling element 91 while X-ray 99 is projected to the entire region of rolling element 91 facing light source 12, and data of the X-ray 99, for one circuit around rolling element 91, i.e. for 360° around rolling element 91, is calculated to generate an image. Therefore, the entirety of rolling element 91 can be inspected without omission, differing from the case where images picked up at a predetermined distance are integrated. Furthermore, since an image is generated based on data of X-ray 99 for one circuit around rolling element 91, inspection can be carried out in a short period of time, differing from the case where images for the integration processing are picked up over a significant period of time. According to the inspection method of rolling element 91 of the present embodiment, the entirety of rolling element 91 can be inspected without omission and in a short period of time. As a result, in the manufacturing method of rolling element 91 of the present embodiment incorporating the above-described inspection method for the inspection step, the inspection step can be implemented efficiently and accurately. Therefore, a rolling element 91 of high reliability can be manufactured economically. Since rolling element 91 obtained by the above-described inspection step is confirmed to be absent of a defect of at least a predetermined size, for example a defect of at least 20 μm in size, a rolling element of high reliability can be achieved.

EXAMPLE

By a rolling element inspection method of the present invention, a ceramic ball employed as a rolling element made of ceramic was inspected for an internal defect. Experiments to examine the sensitivity, accuracy, and the like were carried out. The procedures of the experiments are set forth below.

For an inspection device, the micro X-ray CT directed to experimental animals (Rigaku Corporation) was employed. By a method similar to that of the above-described embodiment, a silicon nitride ceramic ball and a sialon ceramic ball (diameter ⅜ inches) having an internal defect (metal inclusion, hole) were inspected for an inspection time of 17 seconds. From the obtained 3D image data, the position of the defect was identified. Then, the ceramic ball was cut at the identified site for observation of the cross section. For comparison, a similar inspection was carried out for a steel ball (made of JIS SUJ2) of the same size. The results of the experiments are shown in Tables 1 and 2.

TABLE 1

| | | Type of Internal Defect | | | | |
|---|---|---|---|---|---|---|
| | | Metal Inclusion (silicon nitride, sialon) Non-Metal Inclusion (steel material) | | Hole | | Inspection Time |
| | | 20 μm | 30 μm | 20 μm | 30 μm | |
| Material | Silicon Nitride | Detectable | Detectable | Detectable | Detectable | 17 sec. |
| | Sialon | Detectable | Detectable | Detectable | Detectable | 17 sec. |
| | Steel Material (SUJ2) | Non-detectable | Non-detectable | Non-detectable | Non-detectable | 17 sec. |

TABLE 2

| Site | From surface layer | Size | | |
|---|---|---|---|---|
| (from top) | (lateral) | Width | Length | Depth |
| Experimental animal X-ray CT | Approximately 1.9 mm | 400 μm | Approximately 150 μm | |
| Cut, Actual Measurement | Approximately 1.8 mm | 414 μm | Approximately 114 μm | Approximately 138 μm | Approximately 80 μm |

For the silicon nitride ceramics ball and sialon ceramics ball shown in Table 1, metal inclusions and holes of 20 μm and 30 μm in size were detected by an inspection time of 17 seconds. For the steel ball, an X-ray could not pass through. An internal defect could not be detected regardless of the size of the defect.

By comparing the information about the location and size of the defects detected by X-ray CT, and the information about the location and size of the defects by actually cutting the ceramic ball and actually measuring the defect shown in Table 2, it was confirmed that accuracy sufficiently applicable to the inspection of a rolling element for both the location and size was achieved.

For comparison, trials were conducted to detect a defect in a silicon nitride ceramic ball (diameter ⅜ inches) using various inspection methods such as the step type X-ray CT for industrial usage, X-ray transmission inspection by subtraction techniques, inspection by non-linear ultrasonic wave, and inspection by medical X-ray CT. The results of the experiments are shown in Table 3.

TABLE 3

| Inspection Method | Detectable or Not | Inspection Time |
|---|---|---|
| Industrial (step type) X-ray CT | Detectable | 80 minutes |
| X-ray Transmission Inspection by Difference Processing | Detectable | 3 hours |
| Non-linear Ultrasonic Wave | Non-detectable | — |
| Medical X-ray CT | Non-detectable | 40 seconds |

It is appreciated from Table 3 that although a defect could be detected according to the industrial step type X-ray CT inspection and X-ray transmission inspection by difference processing, the inspection time took 80 minutes and 3 hours, respectively, which is time-consuming. In the inspection by non-linear ultrasonic waves, the setting of the inspection conditions such as the way of applying the ultrasonic wave was difficult. A defect could not be detected. The inspection by medical X-ray CT took 40 seconds for the inspection time. However, a defect could not be detected since the slicing distance was 0.5 mm.

It was confirmed by the results of the experiments set forth above that the inspection method of a rolling element made of ceramics of the present invention allowed the entirety of a rolling element made of ceramics to be inspected without omission and in a short period of time, which was difficult to realize by conventional inspection methods.

It should be understood that the embodiments and examples disclosed herein are illustrative and non-restrictive in every respect. The scope of the present invention is defined by the terms of the claims, rather than the description above, and is intended to include any modification within the scope and meaning equivalent to the terms of the claims.

INDUSTRIAL APPLICABILITY

The rolling element inspection method, rolling element manufacturing method, and rolling element of the present invention can be advantageously applied particularly to an inspection method of a rolling element made of ceramics employed as a rolling element for a rolling bearing, a rolling element manufacturing method, and a rolling element.

REFERENCE SIGNS LIST 1 inspection device, 11 holder, 12 light source, 13 detector, 14 calculation unit, 15 image formation unit, 16 defect detector, 91 rolling element, 99 X-ray.

The invention claimed is:

1. An inspection method of a rolling element made of ceramics, comprising the steps of:
projecting an X-ray from a light source to said rolling element, said light source being rotated relatively around said rolling element while said X-ray is simultaneously projected to an entire region of said rolling element facing said light source;
detecting said X-ray passing through said rolling element with a 2D detector, while said light source is rotated relatively around said rolling element;
calculating data of said detected X-ray to generate a 3D image, data of said X-ray for one circuit around said rolling element being calculated to generate said 3D image; and based on said generated 3D image, detecting an internal defect in said rolling element that is a metal inclusion or a hole, wherein during the steps of projecting an X-ray and detecting said X-ray, the light source and the 2D detector rotate around said rolling element while maintaining a positional relationship relative to each other; and wherein the data of said detected X-ray calculated to generate the 3D image includes data of X-rays transmitted through the outer edge portion of the rolling element.

2. The inspection method of a rolling element according to claim 1, wherein said X-ray is projected from said light source having a focal point size less than or equal to 10 μm, at said step of projecting an X-ray.

3. The inspection method of a rolling element according to claim 1, wherein said X-ray spreading conically from said light source is projected to said rolling element, at said step of projecting an X-ray.

4. The inspection method of a rolling element according to claim 1, wherein said ceramics has silicon nitride or sialon as a main component.

5. The inspection method of a rolling element according to claim 1, wherein a defect of at least 20 μm in size is detected at said step of detecting a defect.

6. A manufacturing method of a rolling element comprising the steps of:
   producing a rolling element made of ceramics, and inspecting said rolling element,
   said rolling element being inspected by the inspection method of a rolling element defined in claim 1, at said step of inspecting a rolling element.

7. A rolling element manufactured by the manufacturing method of a rolling element defined in claim 6.

8. The inspection method of a rolling element according to claim 1, wherein the detecting step includes detecting a defect in said rolling element based on said 3D image that would not be detected based on a 2D image generated from data of said X-ray from any single position along the circuit around said rolling element.

* * * * *